United States Patent [19]

Glass et al.

[11] Patent Number: 6,017,902
[45] Date of Patent: Jan. 25, 2000

[54] BORON CONTAINING AMINO ACID COMPOUNDS AND METHODS FOR THEIR USE

[75] Inventors: John D. Glass, Shoreham; Jeffrey A. Coderre, Wading River, both of N.Y.

[73] Assignee: Brookhaven Science Associates, Upton, N.Y.

[21] Appl. No.: 09/258,105

[22] Filed: Feb. 25, 1999

[51] Int. Cl.$^7$ .................................................. A61K 31/69
[52] U.S. Cl. ........................... 514/64; 544/58.1; 562/426
[58] Field of Search .............................. 514/64; 544/58.1; 562/426

[56] References Cited

U.S. PATENT DOCUMENTS

| | | | |
|---|---|---|---|
| 4,332,647 | 6/1982 | Goldenberg | 424/1 |
| 4,587,359 | 5/1986 | Spielvogel et al. | 564/8 |
| 4,824,659 | 4/1989 | Hawthorne | 424/1.1 |
| 4,977,268 | 12/1990 | McPhail et al. | 548/110 |
| 5,466,679 | 11/1995 | Soloway et al. | . |
| 5,599,796 | 2/1997 | Schinazi et al. | 514/44 |
| 5,679,322 | 10/1997 | Wilbur | 424/9.4 |

OTHER PUBLICATIONS

Capala et al., "Accumulation of Boron in Malignant and Normal Cells Incubated In Vitro with Boronophenylalanine, Mercaptoborane or Boric Acid", *Radiation Research*, 146:554–560 (1996).

Coderre et al., "Neutron Capture Therapy of the 9L Rat Glisarcoma Using the P–Boronophenylalanine–Fructose Complex", *Int. J. Radiation Oncology Biol. Phys.*, 30:643–652 (1994).

Coderre et al., "Boron neutron capture therapy for glioblastoma multiforme using p–boronophenylalanine and epithermal neutrons: Trial design and early clinical results", *Journal of Neuro–Oncology*, 33:141–152 (1997).

Ralph G. Fairchild, "Microanalytical techniques for boron analysis using the $^{10}B(n,\alpha)^7Li$ reaction", *Med. Phys.* 13:1 (1986).

Coderre et al., "Selective Delivery of Boron by the Melanin Precursor Analogue p–Boronophenylalanine to Tumors Other Than Melanoma[1]", *Cancer Research*, 50:138–141 (1990).

Miura et al, "Synthesis of a Nickel Tetracarboranylphenylporphyrin for Boron Neutron–Capture Therapy: Biodistribution and Toxicity in Tumor–Bearing Mice", *Int. J. Cancer*, 68:114–119 (1996).

Miura et al, "Biodistribution and Toxicity of 2,4–Divinyl–Nido–*o*–Carboranyldeuteroporphyrin IX in Mice", *Biochemical Pharmacology*, 43:467–476 (1992).

*Primary Examiner*—Peter O'Sullivan
*Attorney, Agent, or Firm*—Margaret C. Bogosian

[57] ABSTRACT

The present invention provides new boron containing amino acid compounds and methods for making these compounds by contacting melphalan or another nitrogen mustard derivative and sodium borocaptate. The present invention also provides a method of treating a mammal having a tumor by administering to the mammal a therapeutically effective amount of the new boron containing amino acid compounds.

32 Claims, 4 Drawing Sheets

BORON CONTAINING AMINO ACID COMPOUNDS AND METHODS FOR THEIR USE

This invention was made with Government support under contract number DE-AC02-98CH10886, awarded by the U.S. Department of Energy. The Government has certain rights in the invention.

BACKGROUND OF THE INVENTION

Cancer is a disease that is the second leading cause of death next to heart attacks in the United States. There has been tremendous research in the development of new compounds and therapies in the treatment of this devastating disease.

Boron neutron-capture therapy (BNCT) is a mode of therapy used in the treatment of cancer. BNCT involves utilizing a boron containing compound that is selectively accumulated in the tumor cell. Once accumulated in the tumor cell, the boron containing compound is irradiated with thermalized neutrons leading to capture of the neutrons and release of high linear-energy-transfer (LET) radiation particles consisting of alpha particles ($^4$He) and lithium ions ($^7$Li). These particles cause direct DNA damage and tumor cell death.

In the clinical setting, BNCT has been used in the treatment of mammals with malignant brain tumors. The treatment involves administering to the mammal a boron containing compound. Preferably, the boronated compound used should have a high intracellular concentration in the tumor, within the radiation volume. Following administration of the boronated compound, the mammal's head is then irradiated in the general area of the brain tumor with an incident beam or field of thermal (<0.5 eV) or epithermal (0.5 eV–10 keV) neutrons. These neutrons become progressively thermalized (average energy≈0.04 eV) as they penetrate deeper into the head. The boron containing nuclei in and around the brain tumor undergo a nuclear reaction immediately after capturing a neutron. This reaction produces high LET radiation particles consisting of alpha particles ($^4$He) and lithium ions ($^7$Li). These particles travel a distance comparable to or slightly less than the diameter of a typical tumor cell and cause the destruction of the tumor cell. (See, Barth et al., 1992).

In order to minimize the destruction of normal (non-tumor) tissue, it is particularly important that there be robust uptake of boron in the tumor relative to normal tissues within the neutron-irradiated target volume. It has been postulated that tumor boron concentrations should be greater than 30 μg B/g (Miura, et al., 1996).

Many classes of compounds have been synthesized for BNCT. For example, U.S. Pat. No. 5,599,796 to Schinazi et al. disclose boron-containing compounds that are sufficiently lipophilic to pass through membranes in a quantity high enough for BNCT. The boron containing compounds disclosed include $Na_2B_{12}H_{11}SH$ (sodium borocaptate or BSH), carboranyl-containing nucleosides and oligonucleotides such as 5-carboranyl-2'-deoxyuridine and 5-o-carboranyl-1-(2-deoxy-2-fluoro-beta-D-arabinofuranosyl) uracil. Other nucleosides and oligonucleotides bearing an -O-[(carboran-1-yl)alkyl]phosphate, S-[(carboran-1-yl)-alkyl]-phosphorothioate, or Se-[(carboran-1-yl)alkyl] phosphoroselenoate in place of the (carboran-1-yl)-phosphonate moiety are disclosed as well.

Boron containing amino acid compounds have also been synthesized for BNCT. For example, U.S. Pat. No. 5,630,786 to Griffin et al. disclose borane anion derivatives that have two polyhedral borane anion cages linked together to form a structure comprising 20 boron atoms used in BNCT. These compounds may be constructed from boron-rich alpha-amino acids or boron enriched oligophosphates.

Efforts have been made to synthesize additional boron containing amino acid analogs and nucleosides used in BNCT. For example, U.S. Pat. No. 5,466,679 to Soloway et al. disclose novel carboranyl uridines including dodecaboran (12)-1-yl)hexyl-2'-deoxyuridine and novel boronated amino acids such as p-(o-carboran-1-yl)-phenylalanine and 5-[6-(1,2-dicarba-closo-dodecaboran(12)-1-ylpentylthio]-2'-deoxyuridine.

Similarly, U.S. Pat. No. 4,587,359 to Spielvogel et al. disclose boron containing nucleosides, nucleotides and amino acids used in BNCT. More particularly, the boron analogs disclosed are amine-carbamoylborane compounds of the formula $R_1 R_2 NHBH_2 C(O)NHR_3$ wherein $R_1$ and $R_2$ are hydrogen or certain alkyl moieties and $R_3$ is an alkyl. These amine-carbamoylborane compounds are prepared by an amine displacement reaction using reactants that are difficult to obtain.

Some boron containing amino acid compounds have been used clinically in BNCT. One such amino acid is p-boronophenylalanine (BPA). This boron containing amino acid has been used at Brookhaven National laboratory Medical Department. BPA has been reported to be minimally toxic to normal tissues and organs. (See Coderre, et al., 1997).

Based on the foregoing, there is still a need for new boron containing amino acid compounds which are readily accumulated in tumor cells, methods of preparing these compounds and methods of using these new boron containing amino acid compounds in BNCT for treating tumors.

SUMMARY OF THE INVENTION

The present invention is a boron containing amino acid compound of the formula:
Structure A (see formula depiction at end of specification) wherein:
$R_1$ is $(CH_2)_2OH$ and $R_2$ is $(CH_2)_2SB_xH_y$; where x is 9 to 12; and y is x−1 or $R_1$ and $R_2$ when taken together with the associated nitrogen atom are:
Structure B
where x is 9 to 12 and y is x−1.

In another embodiment, the invention provides a boron containing amino acid compound of the formula:
Structure C or Structure D The present invention includes a method of treating a mammal having a tumor, comprising administering to the mammal a therapeutically effective amount of a compound of the formula:
Structure A
wherein:
$R_1$ is $(CH_2)_2OH$ and $R_2$ is $(CH_2)_2SB_xH_y$; where x is 9 to 12; and y is x−1 or $R_1$ and $R_2$ when taken together with the associated nitrogen atom are:

Structure B
where x is 9 to 12 and y is x−1 and irradiating the mammal with neutron radiation.

In one preferred embodiment, the method involves treating a mammal having a tumor, comprising administering to the mammal a therapeutically effective amount of a compound of the formula:
Structure C or Structure D
and irradiating the mammal with neutron radiation.

In another preferred embodiment, the method involves treating a mammal having a bone marrow tumor, comprising administering to the bone marrow tumor ex vivo, a therapeutically effective amount of a compound of the formula:
Structure A
wherein:
$R_1$ is $(CH_2)_2OH$ and $R_2$ is $(CH_2)_2SB_xH_y$; where x is 9 to 12; and y is x−1 or $R_1$ and $R_2$ when taken together with the associated nitrogen atom are:
Structure B
where x is 9 to 12 and y is x−1 and irradiating the bone marrow tumor ex vivo with neutron radiation.

In yet another preferred embodiment, the method involves treating a mammal having a bone marrow tumor, comprising administering to the bone marrow tumor ex vivo, a therapeutically effective amount of a compound of the formula:
Structure C or Structure D
and irradiating the bone marrow tumor ex vivo with neutron radiation.

The present invention includes a method of making a compound of the formula:
Structure A
wherein:
$R_1$ is $(CH_2)_2OH$ and $R_2$ is $(CH_2)_2SB_xH_y$; where x is 9 to 12; and y is x−1 or $R_1$ and $R_2$ when taken together with the associated nitrogen atom are:
Structure B
where x is 9 to 12 and y is x−1, comprising contacting an amount of melphalan in an amount of sodium borocaptate $(Na_2B_{12}H_{11}SH)$ sufficient to yield said compound.

The boron containing amino acid compounds of the present invention are preferably derived from nitrogen mustard derivatives. Accordingly in another preferred embodiment, the invention includes a method of making a compound of the formula:
Structure C or Structure D
comprising contacting an amount of melphalan in an amount of sodium borocaptate $Na_2B_{12}H_{11}SH)$ sufficient to yield the compound.

In yet another embodiment, the invention provides a compound of the formula:
Structure A
wherein:
$R_1$ is $(CH_2)_2OH$ and $R_2$ is $(CH_2)_2SB_xH_y$; where x is 9 to 12; and y is x−1 or $R_1$ and $R_2$ when taken together with the associated nitrogen atom are:
Structure B
where x is 9 to 12 and y is x−1, prepared by contacting an amount of a nitrogen mustard derivative in an amount of sodium borocaptate $(Na_2B_{12}H_{11}SH)$ sufficient to yield said compound.

Preferred compounds of the present invention have the formula:
Structure C or Structure D
and are prepared by contacting an amount of melphalan in an amount of sodium borocaptate $(Na_2B_{12}H_{11}SH)$ sufficient to yield said compound.

One advantage of the compounds of the present invention is that they have a high boron content which allows for a high yield radiation particles consisting of alpha particles ($^4He$) and lithium ions ($^7Li$) upon irradiating the mammal with neutron radiation. This is a practical advantage over the boron containing compounds of the prior art.

Another advantage of the amino acid compounds of the present invention is that they selectively accumulate in tumor cells as opposed to normal cells. This allows for selective destruction of tumor tissue with minimal disruption of normal tissues upon irradiation with neutrons.

Yet another advantage of the present invention is to provide boron containing amino acid compounds for BNCT that are active at lower doses as compared to other boron containing compounds known presently in the art of cancer treatment.

Still another advantage of the compounds of the present invention is that they can easily be prepared using starting reactants that are commercially available. Preferably, the starting reactant includes a nitrogen mustard derivative.

For a better understanding of the present invention together with other and further advantages, reference is made to the following description taken in conjunction with the examples, the scope of which is set forth in the appended claims.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawing, wherein.

DETAILED DESCRIPTION OF THE INVENTION

Figure 1:
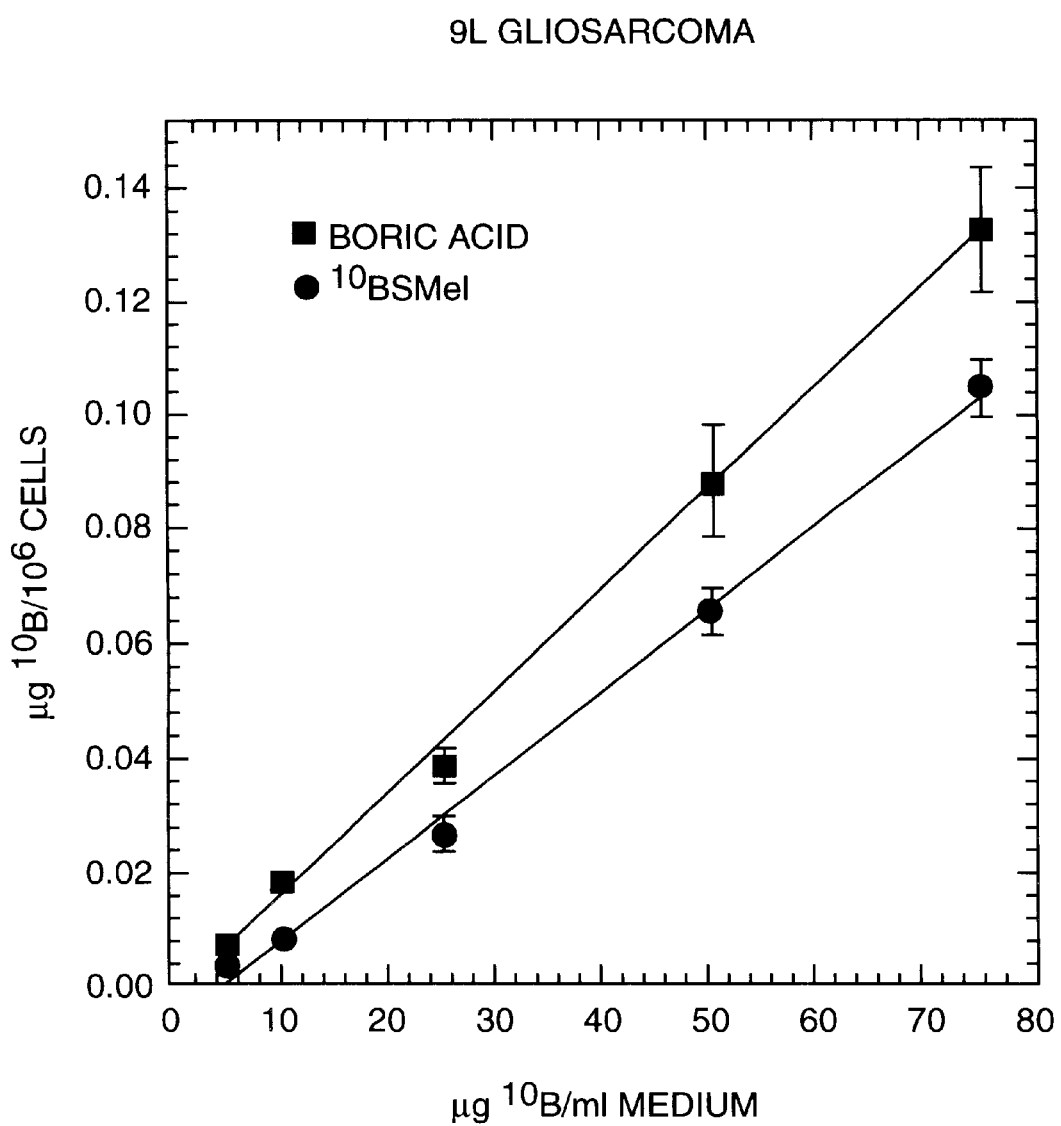
FIG. 1 is a graphic illustration of intracellular accumulation of boron ($^{10}B$) for BSMel (identified as Structure C or Structure D) and boric acid in 9 L rat gliosarcoma cells. The slope of the boric acid line is used as a control indicating uniform intracellular and extracellular boron concentration.

The boron containing amino acid compounds of the present invention have the general formula:

Structure A
wherein:
$R_1$ is $(CH_2)_2OH$ and $R_2$ is $(CH_2)_2SB_xH_y$; where x is 9 to 12; and y is x−1 or $R_1$ and $R_2$ when taken together with the associated nitrogen atom are:
Structure B
where x is 9 to 12 and y is x−1.

Preferably, $R_1$ and $R_2$ when taken separately each include an alkyl group of at least two carbons. As used herein, all groups contain straight or branched, saturated or unsaturated carbon chains, having at least two carbon atoms. Some examples of alkyl groups are methyl, ethyl, propyl, butyl, isobutyl, n-butyl, secondary butyl, tertiary butyl, and benzyl.

The present invention includes boron containing amino acid compounds having at least one borane cage moiety. The borane cage moiety contains boron and hydrogen atoms in the general formula $B_xH_y$, where x is 9 to 12 and y is x−1. Examples of borane cage moieties include decaborane ($B_{10}H_9$), undecaborane ($B_{11}H_{10}$) and dodecaborane $B_{12}H_{11}$). Particularly preferred compounds of the present invention have a dodecaborane cage bonded to the sulfur group.

The most preferred boron containing amino acid compounds of the present invention have the formula:
Structure C or Structure D It will be understood by those skilled in the art that although nitrogen is shown in the para position relative to alanine on Structures A, C and D, the present invention encompasses compounds with nitrogen at the ortho or meta positions relative to alanine on the benzene ring.

As used herein, BSMel or $^{10}$BSMel refers to the most preferred boron containing amino acid compounds of the present invention having the formula:
Structure C or Structure D It will be understood that the present invention includes any enantiomeric form of BSMel including the racemates or racemic mixture of BSMel. In some cases, there may be advantages, i.e. greater efficacy, to using a particular enantiomer when compared to the other enantiomer or racemate or racemic mixture of the present invention and such advantages can be readily determined by those skilled in the art.

The present invention embraces salts of the new boron containing amino acid compounds, including acid-addition and metal salts. Such salts are formed by well known procedures with pharmaceutically acceptable and pharmaceutically unacceptable acids and metals. By "pharmaceutically acceptable" it is meant those salt-forming acids and metals which do not substantially increase the toxicity of the compound.

Some examples of suitable salts include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g. p-toluenesulfonic acids, and the like. The pharmaceutically unacceptable acid addition salts, while not useful for therapy, are valuable for isolation and purification of the new substances. Further, they are useful for the preparation of pharmaceutically acceptable salts. Of this group, the more common salts include those formed with hydrofluoric and perchloric acids. Hydrofluoride salts are particularly useful for the preparation of the pharmaceutically acceptable salts, e.g. the hydrochlorides, by solution in hydrochloric acid and crystallization of the hydrochloride salt formed. The perchloric acid salts are useful for purification and crystallization of the new compounds.

Whereas all metal salts may be prepared and are useful for various purposes, the pharmaceutically acceptable metal salts are particularly valuable because of their utility in therapy. The pharmaceutically acceptable metals include more commonly sodium, potassium and alkaline earth metals of atomic number up to and including 20, i.e., magnesium and calcium and additionally, aluminum, zinc, iron and manganese, among others. Of course, the metal salts include complex salts, i.e. metal chelates, which are well recognized in the art.

The new boron containing amino acid compounds of the present invention or salts thereof may be prepared using starting reactants that are readily available. The present invention includes a method of making a compound of the formula:
Structure A
wherein:
$R_1$ is $(CH_2)_2OH$ and $R_2$ is $(CH_2)_2SB_xH_y$; where x is 9 to 12; and y is x−1 or $R_1$ and $R_2$ when taken together with the associated nitrogen atom are:
Structure B
where x is 9 to 12 and y is x−1, comprising contacting an amount of a nitrogen mustard derivative in an amount of sodium borocaptate ($Na_2B_{12}H_{11}SH$) sufficient to yield said compound.

Preferably the starting reactant includes a nitrogen mustard derivative. As used herein, a nitrogen mustard derivative includes compounds having $C_5H_{11}Cl_2N$ or a nitrogen mustard substituent. Some examples of nitrogen mustard derivatives are melphalan, melphalan (D-isomer of melphalan), merphalan (DL-isomers of melphalan), chlorambucil ($C_{14}H_{19}Cl_2NO_2$), cyclophosphamide ($C_7H_{15}Cl_2N_2O_2P$), CCNU ($C_9H_{16}Cl\ N_3O$), cisplatin ($Cl_2H_6N_2Pt$), and the like.

Accordingly, in the most preferred embodiment, the present invention includes a method of making a compound of the formula:
Structure C or Structure D
comprising contacting an amount of melphalan in an amount of sodium borocaptate ($Na_2B_{12}H_{11}SH$) sufficient to yield or produce the compound.

Melphalan, or phenylalanine nitrogen mustard, is a commonly used antineoplastic agent that kills tumor cells by alkylation (cross-linking) of double-stranded DNA. Melphalan exhibits the following structure:
Structure E As used herein, melphalan is 4-[Bis-(2-chloroethyl)amino]-L-phenylalanine or $C_{16}H_{18}Cl_2N_2O_2$. Melphalan is available from Sigma Chemical Company, U.S.A.

Sodium borocaptate ($Na_2B_{12}H_{11}SH$) or BSH, is a highly enriched dodecaborane compound containing greater than about 95% B-10. Sodium borocaptate is available from Boron Biologicals, Inc., U.S.A. and is a source of boron for the compounds of the present invention.

The present invention includes contacting or reacting an amount of a nitrogen mustard derivative with an amount of sodium borocaptate sufficient to yield or produce the compounds of the present invention. As used herein, the term "an amount sufficient" is the minimum amount of reactant needed to yield or produce the boron containing amino acid compounds of the present invention. This amount can vary depending on the amount of reactants used. In any event, the practitioner is guided by skill and knowledge in the field, and the present invention includes without limitation amounts of reactants which are effective to achieve the desired yields.

Preferably, sodium borocaptate is contacted with melphalan or another nitrogen mustard derivative in a ratio of preferably about two parts of sodium borocaptate to about one part of melphalan or another nitrogen mustard derivative, more preferably about three parts of sodium borocaptate to about one part of melphalan or another nitrogen mustard derivative and most preferably, about 800 mg of sodium borocaptate is contacted with about 200 mg of melphalan or another nitrogen mustard derivative.

In one embodiment, the present invention includes dissolving sodium borocaptate and suspending melphalan or another nitrogen mustard derivative in a suitable solvent. Suitable solvents include water, sodium carbonate, sodium bicarbonate ($NaHCO_3$), sodium chloride and the like. Most preferably, the suitable solvent is aqueous sodium bicarbonate solution.

As used herein "an amount" of sodium bicarbonate is that amount sufficient to dissolve sodium borocaptate and suspend melphalan or another nitrogen mustard derivative. Preferably, from about 1 ml to about 3 L of sodium bicarbonate, more preferably from about 10 ml to about 2 L and most preferably, from about 10 ml to about 100 ml of sodium bicarbonate solution is used.

The sodium bicarbonate solution used in the present invention is at a concentration of preferably, from about 100 mg to about 20 g of sodium bicarbonate per 100 ml of water, more preferably, from about 100 mg to about 20 g of sodium bicarbonate per 100 ml of water and most preferably, from about 3 g to about 5 g of sodium bicarbonate per 100 ml of water is used to dissolve sodium borocaptate and suspend melphalan or another nitrogen mustard derivative.

Preferably melphalan or another nitrogen mustard derivative is contacted with a suitable solvent. Preferably, the solvent will dissolve the nitrogen mustard derivative into a suspension where the nitrogen mustard derivative is dispersed in the suitable solvent.

It will be understood by those skilled in the art that the order of contacting or mixing the reactants can be in any order. For example, melphalan or another nitrogen containing derivative, can be contacted with sodium borocaptate to yield a compound of the present invention. Alternately, sodium borocaptate can be contacted with melphalan or another nitrogen mustard derivative, to yield a compound of the present invention. In one embodiment, sodium bicarbonate can be contacted with sodium borocaptate, then melphalan or another nitrogen mustard derivative, to yield a compound of the present invention.

After dissolving sodium borocaptate and melphalan or another nitrogen mustard derivative in sodium bicarbonate solution, the sodium borocaptate undergoes alkylation at the nitrogen group of melphalan. This is shown in Reaction Scheme I and Reaction Scheme II (see page before claims). Preferably, the reaction occurs at about normal atmospheric pressure (760 mm Hg) and at room temperature or from about 15° C. to 40° C.

The alkylation reaction results in the precipitation of the boron containing amino acid compounds of the present invention out of solution. Most preferably, the precipitation reaction occurs at temperature of between about 2° C. to about 10° C. or refrigeration temperature.

The precipitation reaction is increased by adding an acidifying agent. Some examples of suitable acidifying agents are mineral acids such as hydrochloric, hydriodic, hydrobroric, phosphoric, metaphosphoric, nitric and sulfuric acids. Most preferably, hydrochloric acid is used as the acidifying agent.

Preferably, the acidifying agent is added after dissolving sodium borocaptate and suspending melphalan in sodium bicarbonate solution. More preferably, the solution is acidified to a pH of from about one to about six, and most preferably the pH is from about two to about three.

After preparation, the novel compounds of the present invention can be conveniently purified by standard methods known in the art. Some suitable examples include centrifugation, crystallization from a suitable solvent or partition-column chromatography.

The percentage of boron by weight in the amino acid compounds of the present invention varies with the particular compound. As an example, BSMel contains about 28% boron by weight.

In another embodiment, the present invention is directed to a method of treating a mammal having a tumor, comprising administering to the mammal a therapeutically effective amount of a compound of the formula:
Structure A
wherein:
$R_1$ is $(CH_2)_2OH$ and $R_2$ is $(CH_2)_2SB_xH_y$; where x is 9 to 12; and y is x−1 or $R_1$ and $R_2$ when taken together with the associated nitrogen atom are:
Structure B
where x is 9 to 12 and y is x−1 and irradiating the mammal with neutron radiation.

In the most preferred embodiment, the present invention includes a method of treating a mammal having a tumor, comprising administering to the mammal a therapeutically effective amount of a compound of the formula:
Structure C or Structure D
and irradiating the mammal with neutron radiation.

The new boron containing amino acid compounds of the present invention can be used in vivo, in vitro, and ex vivo, for example, in living mammals as well as in cultured tissue, organ or cellular systems. Mammals include, for example, humans, as well as pet animals such as dogs and cats, laboratory animals, such as rats and mice, and farm animals, such as horses and cows. Tissues, as used herein, are an aggregation of similarly specialized cells which together perform certain special functions. Cultured cellular systems include any mammalian cells, such as epithelial, endothelial, red blood, and white blood cells. More particularly, gliosarcoma, melanoma, leukemia, bone marrow cells, lymphoma cells, and the like.

Ex vivo use of the compounds of the present invention, permits the purging of tumors or cancers from the bone marrow. In hematopoietic and lymphopoietic cancers, for example, a portion of the bone marrow having the cancer or tumor is removed from the mammal. Subsequently, the bone marrow cancer or tumor is treated with a compound of the present invention and irradiated with neutrons (ex vivo) or outside of the mammal. This leads to capture of the neutrons by the boron containing compound and release of high linear-energy-transfer (LET) radiation particles consisting of alpha particles ($^4$He) and lithium ions ($^7$Li). These particles kill the cancer cells or tumor cells and thereby purge the cancer or tumor from the bone marrow. Using immunological techniques, the mammal's own purged marrow is transplanted back into the mammal. This method avoids graft-versus-host disease, finding a histocompatible match and other serious complications of allogenic marrow grafts. Additionally, the method of the present invention permits ex vivo localized treatment of the mammal. Thus, treatment is directed specifically at the site of the cancer or tumor. This treatment avoids bone marrow suppression and allows higher doses of adjunct conventional radiation and chemotherapy to kill the remaining cancer as determined by those skilled in the medical arts. (For a review see, Sieber et al., 1984)

The present invention is directed to a method for treating a mammal having a tumor. As used herein a tumor is a new growth of tissue where cell multiplication is uncontrolled. Tumors can be benign and malignant. Benign tumors are localized and usually do not spread to other sites. Most benign tumors are not fatal. By contrast, malignant tumors or cancers invade and destroy adjacent cells and spread to distant sites. This endogenous spread of cancer is often fatal.

Some examples of cancers include sarcoma, lymphoma, leukemia, gliosarcoma, melanoma, and the like. Cancer can occur in different areas of the body, for example, in the bone, brain, liver, lung, pancreas and other organs.

The present invention includes administering a therapeutically effective amount of the new boron containing compounds of the present invention. As used herein, a therapeutically effective amount is that amount effective to achieve the specified result of treating the tumor or cancer. Preferably, the boron containing amino acid compound is provided to the tumor cell in an amount which destroys tumor tissue without disruption of normal tissue function when irradiated with neutrons. Most preferably, the tumor destruction occurs without the serious side effects that may be observed in conventional tumor therapy, such as radiotherapy or chemotherapy. Some serious side effects include bone marrow suppression, anemia and infection.

The maximal dosage for treating a mammal having a tumor is the highest dosage which does not cause undesirable or intolerable side effects. Minimal dosage is the lowest dosage where efficacy is first observed. For example, the boron containing amino acid compounds of the present invention can be administered in an amount which provides $^{10}$B concentrations in tumor tissues of about 30 µg/g or greater. Moreover, since the boron containing amino acid compounds of the present invention are highly accumulated in tumor cells, a lower dosage can be used. In any event, the practitioner is guided by skill and knowledge in the field, and the present invention includes without limitation dosages which are effective to achieve the described effect.

As previously stated, the boron containing amino acids compounds of the present invention have a high affinity for tumor cells as opposed to normal cells. Therefore, a lower dosage of the boron containing amino acid compound can be administered to achieve tumor-to-normal-tissue boron concentration ratios of preferably, greater than about two to one, more preferably greater than three to one, and most preferably greater than about four to one.

The method of the present invention includes administering or providing new boron containing amino acid compounds in an amount which is effective for treating tumors or cancers in mammalian cells or a mammal. Administering the boron compounds can be accomplished in a variety of ways. In cultured cellular systems (in vitro or ex vivo), the new boron containing amino acid compounds can be administered by contacting the cells directly with a therapeutically effective amount of the compound.

In living mammals (in vivo), boron compounds of the present invention can be administered systemically by the parenteral and enteral routes. For example, boron compounds of the present invention can easily be administered intravenously (e.g., intravenous injection) which is a preferred route of delivery. Intravenous administration can be accomplished by contacting the boron compounds in a suitable pharmaceutical carrier (vehicle) or excipient as understood by practitioners in the art.

Oral or enteral use is also contemplated, and formulations such as tablets, capsules, pills, troches, elixirs, suspensions, syrups, wafers, chewing gum and the like can be employed to provide the boron containing amino acid compounds of the present invention.

Alternatively, delivery of the boron containing amino acid compound can include topical application. Accordingly, the carrier is preferably suited for topical use. Compositions deemed to be suited for such topical use include gels, salves, lotions, creams ointments and the like.

After the boron containing amino acid compounds are administered, and the compound is taken up by the tumor cells, the mammal is irradiated with thermal neutron radiation in BNCT. Preferably, the thermal neutrons are produced by application of an external neutron beam from a small nuclear reactor.

As previously stated, BNCT is a mode of antitumor bimodal radiation therapy which utilizes the ability of the stable, non-radioactive nuclide boron-10 ($^{10}$B) to absorb thermalized neutrons.

More specifically, in BNCT of tumors following the methods of the present invention, the mammal is given a boron containing amino acid compound of Structure A or Structure C or Structure D. These compounds are highly enriched in the $^{10}$B isotope. Tumor cells accumulate the boron compound within the effective irradiation volume. The tumor area is then irradiated with preferably thermalized neutrons, some of which are captured by the boron-10 concentrated in the tumor. Preferably, the $^{10}$B concentrations in tumor tissues is greater than 30 µg/g so that the neutrons captured by the boron-10 nuclide is higher, compared to the capture by other nuclides normally present in mammalian tissues.

Boron-10 undergoes the following nuclear reaction when it captures a thermal neutron:

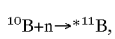

In this nuclear reaction, a $^{10}B$ nucleus absorbs a neutron, forming the metastable nuclide $*^{11}B$, that spontaneously and nearly instantaneously disintegrates into $^4He$ and $^7Li$ particles, which together possess an average total kinetic energy of 2.34 MeV. These ionized particles travel about $7\pm2$ μm, or the approximate diameter of the tumor cells. Accordingly, the $^4He$ and $^7Li$ particles destroy the tumor cell and not the surrounding normal cells. In effect, the tumor alone is irradiated with $^4He$ and $^7Li$ particles. Therefore, the efficacy of BNCT resides in the production of highly localized, ionizing radiation within the targeted tissues. In this manner, the tumor can receive a preferentially large radiation dose compared to that received by the surrounding and contiguous non-tumorigenic or normal tissue.

EXAMPLES

Examples have been set forth below for purpose of illustration and to describe the best mode of the invention at the present time. The scope of the invention is not to be in any way limited by the examples set forth herein.

Example 1

Synthesis of $^{10}BSMel$

In this example, a widely used metabolite analog (melphalan or 4-[bis(2-chloroethyl)amino]-L-phenylalanine) that kills tumor cells by alkylation (crosslinking) of double-stranded DNA is converted to a metabolite analog containing a high B-10 content for use as a boron delivery agent for neutron capture therapy. The new metabolite analog (BSMel) retains the capacity to be actively accumulated by malignant cells, notably leukemia and lymphoma cells.

$^{10}BSH$ (880 mg) was dissolved in 30 ml of 5% sodium bicarbonate solution. Melphalan (213 mg) was added and the solution was stirred vigorously in a stoppered tube. After about 2 hours, most of the melphalan had dissolved and a fine white precipitate began to form. After about 48 hours the reaction mixture was placed in the refrigerator overnight to complete separation of a fine white solid. The precipitate was collected by centrifugation and dissolved in 30 ml water with heating to the boiling point. The hot solution was cooled to room temperature and a small amount of insoluble material was removed by centrifugation. Acidification of the solution to pH 2.7 with HCL caused heavy precipitation of the product, which was completed by storage in the refrigerator overnight. The product was collected by centrifugation and washed with water resuspension and centrifugal sedimentation. The washed centrifugal pellet was frozen and dried by lyophilization to yield 120–160 mg of $^{10}BSMel$. The compound contains a single dodecaborane cage rather than the two cages that would result from substitution of both arms of the nitrogen mustard group. From the known propensity of BSH to undergo dialkylations and from the symmetry of the proton NMR spectrum of the product, we show that BSMel is the bicyclic compound resulting from alkylation of a single BSH molecule by both arms of the nitrogen mustard group of a melphalan molecule. $^{10}BSMel$ is an aromatic amino acid derivative monosubstituted with the $B_{12}H_{11}$ cage. The synthesis reaction is shown in Reaction Scheme II.

Additionally, BSMel is soluble in neutral to weakly alkaline aqueous solutions, but precipitates when the solutions are acidified. BSMel is prepared from sodium borocaptate (about 95% of the boron is enriched in B-10 isotope), and contains about 28% boron by weight. BSMel migrates as a single ninhydrin-positive spot on TLC, and shows a single boron containing spot corresponding to the ninhydrin reactive zone by neutron track etching methods.

Example 2

Measurement of $^{10}BSMel$ Uptake in Gliosarcoma Cells

Cultured 9 L rat gliosarcoma (GS-9 L) cells were equilibrated for 2 hr with medium containing graded doses of boric acid and $^{10}BSMel$, then stripped of extracellular medium by centrifugation through an oil layer, using the procedures of Capala et al., 1996. B-10 was then measured in the cellular fraction by direct current plasma atomic emission spectroscopy. Since boric acid has been shown to equilibrate freely between intracellular and extracellular volumes under these experimental conditions, boric acid controls are used to establish a line representing no active accumulation and no exclusion of boron. A slope greater than that for boric acid represents active accumulation of boron above the concentration in the medium and a slope below that for boric acid represents exclusion of boron from the intracellular space. The results of this example are shown in FIG. 1, which is a graphic illustration of intracellular accumulation of boron ($^{10}B$) for BSMel and boric acid in 9 L rat gliosarcoma cells.

Example 3

Measurement of $^{10}BSMel$ Uptake in Melanoma Cells

Figure 2:
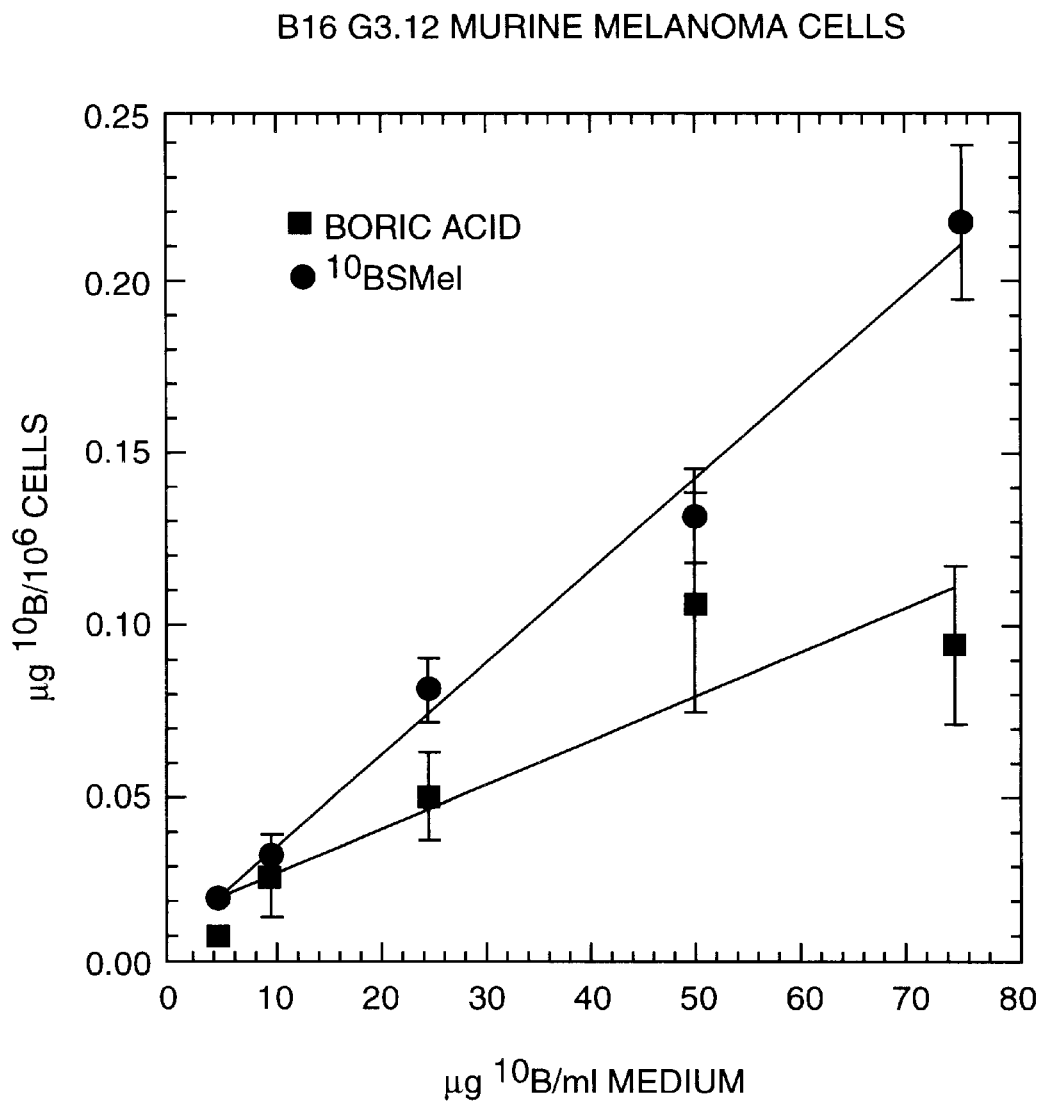
FIG. 2 is a graphic illustration of intracellular accumulation of boron ($^{10}B$) for BSMel (identified as Structure C or Structure D) and boric acid in E16G3.12 pigmented murine melanoma cells. The slope of the boric acid line is used as a control indicating uniform intracellular and extracellular boron concentration.

Cultured B16G3.12 pigmented murine melanoma cells were equilibrated for 2 hr with medium containing graded doses of boric acid and $^{10}BSMel$, then stripped of extracellular medium by centrifugation through an oil layer, using the procedures of Capala et al., 1996. B-10 was then measured in the cellular fraction by direct current plasma atomic emission spectroscopy. Since boric acid has been shown to equilibrate freely between intracellular and extracellular volumes under these experimental conditions, boric acid controls are used to establish a line representing no active accumulation and no exclusion of boron. A slope greater than that for boric acid represents active accumulation of boron above the concentration in the medium and a slope below that for boric acid represents exclusion of boron from the intracellular space. The results of this example are shown in FIG. 2, which is a graphic illustration of intracellular accumulation of boron ($^{10}B$) for BSMel and boric acid in B16G3.12 pigmented murine melanoma cells. The slope of the boric acid line is used as a control indicating uniform intracellular and extracellular boron concentration.

Example 4

Measurement of $^{10}BSMel$ Uptake in Leukemia Cells

Figure 3:
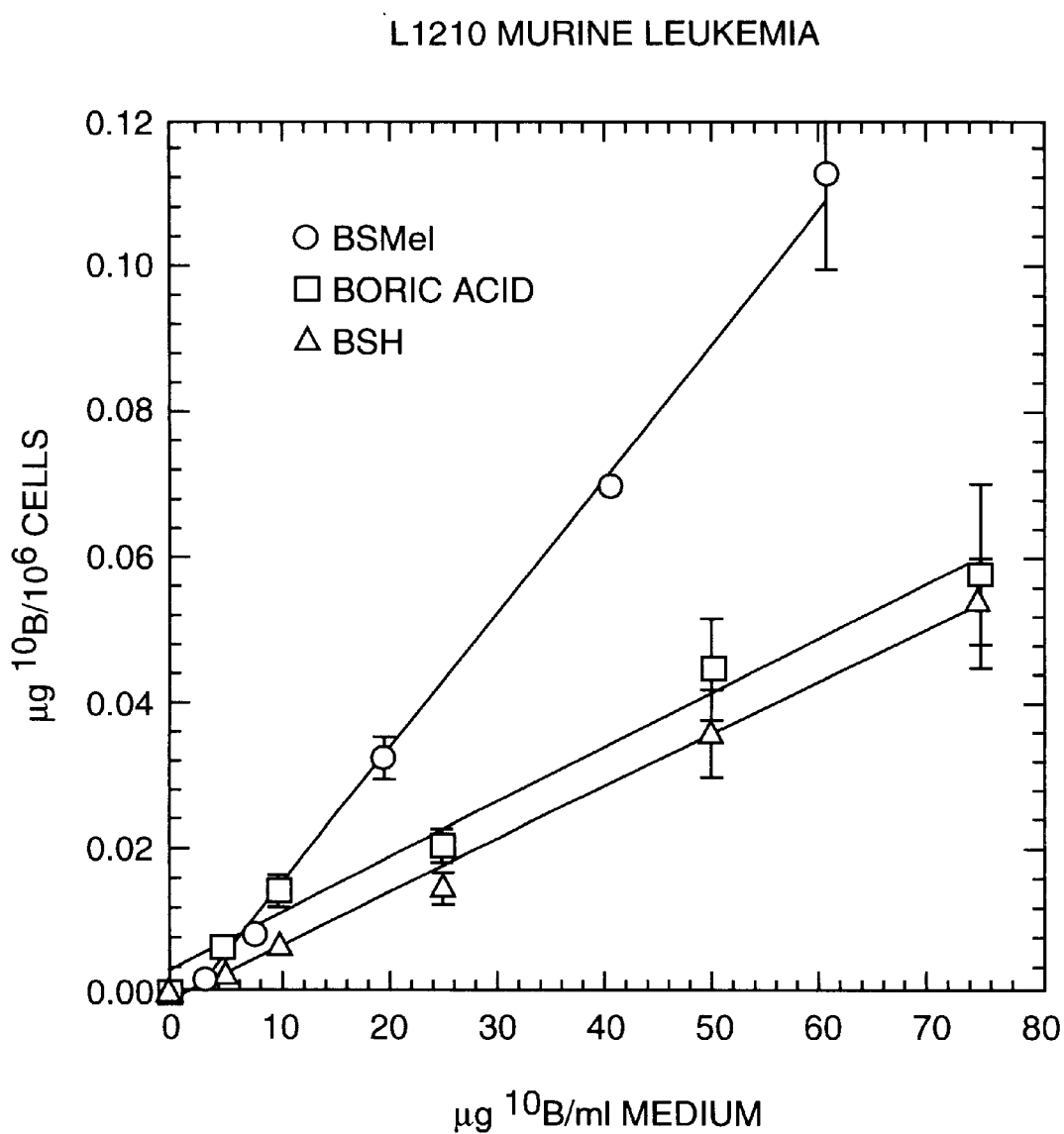
FIG. 3 is a graphic illustration of intracellular accumulation of boron ($^{10}B$) for BSMel (identified as Structure C or Structure D), boric acid and BSH in L1210 murine leukemia cells. The slope of the boric acid line is used as a control indicating uniform intracellular and extracellular boron concentration.

Cultured L1210 murine leukemia cells (ATCC accession number CCL-219) were equilibrated for 2 hr with medium containing graded doses of $^{10}BSMel$, boric acid and BSH, then stripped of extracellular medium by centrifugation through an oil layer, using the procedures of Capala et al., 1996. B-10 was then measured in the cellular fraction by direct current plasma atomic emission spectroscopy. Since boric acid has been shown to equilibrate freely between intracellular and extracellular volumes under these experimental conditions, boric acid controls are used to establish a line representing no active accumulation and no exclusion of boron. A slope greater than that for boric acid represents active accumulation of boron above the concentration in the medium and a slope below that for boric acid represents exclusion of boron from the intracellular space. The results of this example are shown in FIG. 3, which is a graphic illustration of intracellular accumulation of boron ($^{10}$B) for BSMel, boric acid and BSH in L1210 murine leukemia cells. The slope of the boric acid line is used as a control indicating uniform intracellular and extracellular boron concentration.

Example 5

Measurement of $^{10}$BSMel Uptake in Lymphoma Cells

Figure 4:
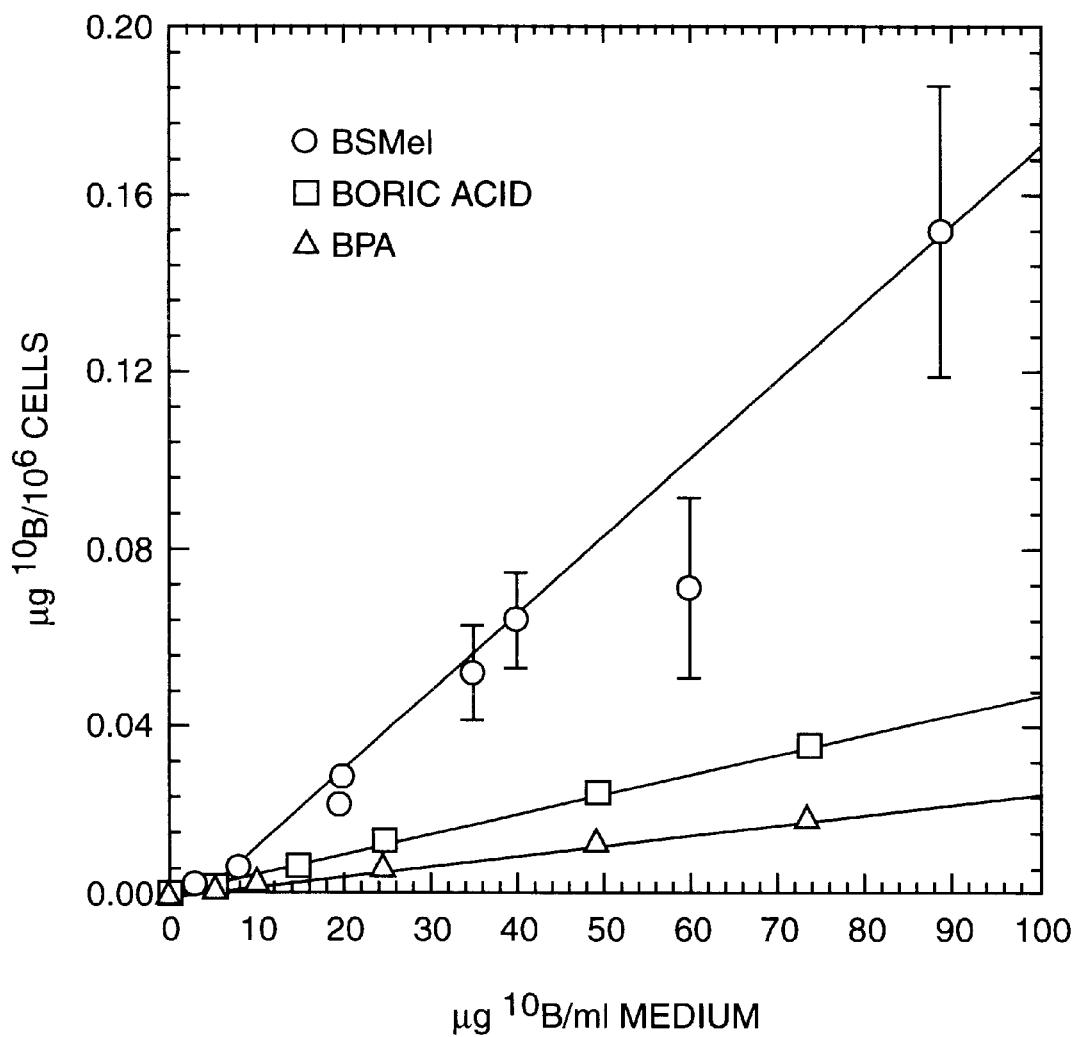
FIG. 4 is a graphic illustration of intracellular accumulation of boron ($^{10}B$) for BSMel (identified as Structure C or Structure D), boric acid and BPA in L5178Y murine lymphoma cells. The slope of the boric acid line is used as a control indicating uniform intracellular and extracellular boron concentration.

Cultured L5178Y murine lymphoma cells (ATCC accession number CRL-9518) were equilibrated for 2 hr with medium containing graded doses of $^{10}$BSMel, boric acid and BPA, then stripped of extracellular medium by centrifugation through an oil layer, using the procedures of Capala et al., 1996. B-10 was then measured in the cellular fraction by direct current plasma atomic emission spectroscopy. Since boric acid has been shown to equilibrate freely between intracellular and extracellular volumes under these experimental conditions, boric acid controls are used to establish a line representing no active accumulation and no exclusion of boron. A slope greater than that for boric acid represents active accumulation of boron above the concentration in the medium and a slope below that for boric acid represents exclusion of boron from the intracellular space. The results of this example are shown in FIG. 4, which is a graphic illustration of intracellular accumulation of boron ($^{10}$B) for BSMel, boric acid and BPA in L5178Y murine lymphoma cells. The slope of the boric acid line is used as a control indicating uniform intracellular and extracellular boron concentration.

In summary, Examples 2–5 clearly show that $^{10}$BSMel is strongly taken up by L1210 murine leukemia cells and L5178 murine lymphoma cells, but not by GS-9L rat gliosarcoma cells or by B16G3.12 murine melanoma cells. The observed uptake in murine leukemia and lymphoma cells is comparable to that reported for BPA with regards to uptake in rat GS-9L gliosarcoma cells. (See Coderre et al., 1994). The results of Examples 2–5 show that the boron containing amino acid compounds of the present invention are useful for BNCT.

BIBLIOGRAPHY

1. Barth, R. F, Soloway, A. H., Fairchild, R. G., Brugger, R. M., "Boron Neutron Capture Therapy," *Cancer*, 70:2995–3008 (1992).
2. Capala, J., Maker, M. S., Coderre, J. A., Accumulation of boron in malignant and normal cells incubated in vitro with boronophenylalanine, mercaptoborane or boric acid, *Radiat. Res.*, 146:554–560, 1996.
3. Coderre, J. A., T. M. Button, P. L. Micca, C. D. Fisher, M. M. Nawrocky and H. B. Liu, Neutron capture therapy of the 9 L rat gliosarcoma using the p-boronophenylalaninifructose complex, *Int. J Radiat. Oncol. Biol. Phys.*, 30:643–652, 1994.
4. Coderre, J. A., Elowitz, E., Chadha, M., Bergland, R., Capala, J., Joel, D. D., Liu, H. B., Slatkin, D. N. and Chanana, A. D., Boron neutron capture therapy of glioblastoma multiforme using p-boronophenylalanine and epithermal neutrons: Trial design and early clinical results. *J. NeuroOncol* 33, 141–152 (1997).
5. Coderre, J. A., Glass, J. D., Fairchild, R. G., Micca, P. L., F and, I., and Joel, D. D., Selective delivery of boron by the melanin precursor analogue p-boronophenylalanine to tumors other than melanoma, *Cancer Res.*, 50, 138–141 (1990).
6. Fairchild, R. G., Gabel, D., Laster, B. H., Greenberg, D., Kiszenick, W., and Micca, P. L., Microanalytical techniques for boron analysis using the $^{10}$B(n,)$^7$Li reaction. *Med Phys.*, 13, 50–56 (1986).
7. Miura, M., Micca, P. L, Fisher, C. D., Heinrichs, J. C., Donaldson, J. A., Finkel, G. C., and Slatkin, D. N., Synthesis of a nickel tetracarboranylphenylporphyrin for boron neutron-capture therapy: Biodistribution and toxicity in tumor-bearing mice, *Int. J Cancer:* 68, 114–119 (1996).
8. Miura, M., Micca, P. L., Heinrichs, J. C., Gabel, D., Fairchild, R. G. and Slatkin, D. N., Biodistribution and toxicity of 2,4-divinyl-nido-o-carboranyldeuteroporphyrin IX in mice, *Biochem. Pharm.*, 43, 467–476, (1992).
9. Sieber, F., Spivak, J. L., Sutcliffe, A. M., Selective killing of leukemic cells by merocyanine 540-mediated photosensitization, *Proc. Natl. Acid Sci. USA*, 81, 7584–7587, (1984).

Thus, while there have been described what are presently believed to be preferred embodiments of the present invention, those skilled in the art will realize that other and further modifications and changes can be made without departing from the true spirit of the invention, and it is intended to include all such changes and modifications as come within the scope of the invention as pointed out in the claims appended hereto.

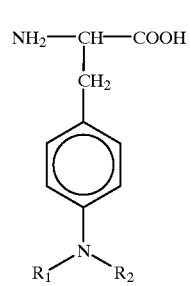

Structure A

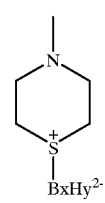

Structure B

-continued

Structure C

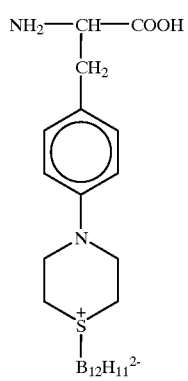

Structure D

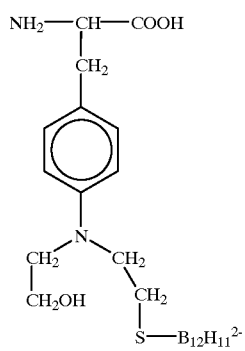

Structure E

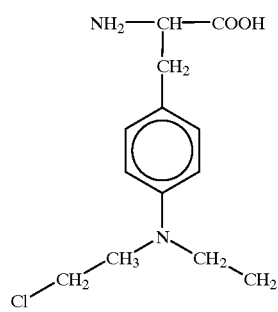

Reaction Scheme I

Na₂B₁₂H₁₁SH + Solvent +

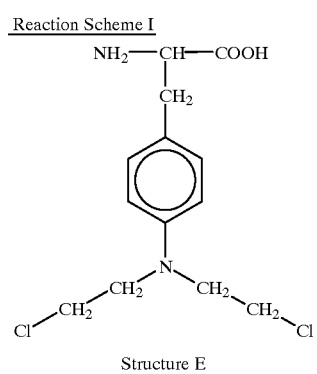

Structure E

-continued

Structure A

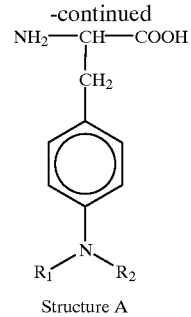

Reaction Scheme II

Na₂B₁₂H₁₁SH + NaHCO₃ +

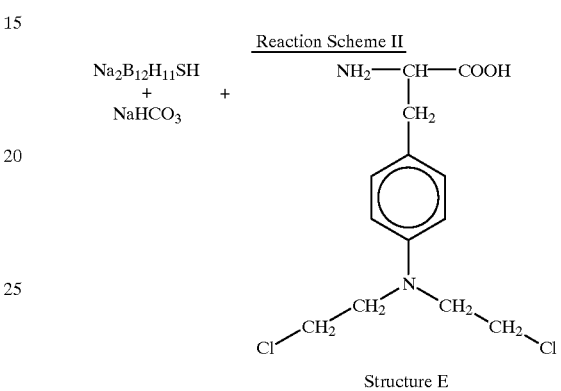

Structure E

↓

Structure C

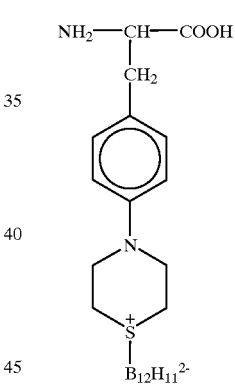

or

Structure D

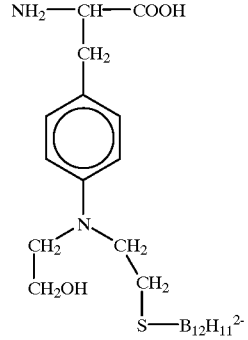

We claim:

1. A compound of the formula:
Structure A
   wherein:
   $R_1$ is $(CH_2)_2OH$ and $R_2$ is $(CH_2)_2SB_xH_y$; where x is 9 to 12; and y is x−1 or $R_1$ and $R_2$ when taken together with the associated nitrogen atom are:
Structure B
   where x is 9 to 12 and y is x−1.

2. A compound of the formula:
Structure C or Structure D.

3. A method of treating a mammal having a tumor, comprising administering to the mammal a therapeutically effective amount of a compound of the formula:

Structure A wherein:

$R_1$ is $(CH_2)_2OH$ and $R_2$ is $(CH_2)_2SB_xH_y$; where x is 9 to 12; and y is x−1 or $R_1$ and $R_2$ when taken together with the associated nitrogen atom are:

Structure B where x is 9 to 12 and y is x−1 and irradiating the mammal with neutron radiation.

4. A method of treating a mammal having a tumor, comprising administering to the mammal a therapeutically effective amount of a compound of the formula:

Structure C or Structure D and irradiating the mammal with neutron radiation.

5. A method according to claim 3, wherein the compound is administered orally, parenterally or topically to the mammal.

6. A method according to claim 4, wherein the compound is administered orally, parenterally or topically to the mammal.

7. A method according to claim 3, wherein the tumor is a cancer.

8. A method according to claim 4, wherein the tumor is a cancer.

9. A method according to claim 7, wherein the cancer is leukemia, lymphoma, gliosarcoma, melanoma or bone marrow cancer.

10. A method according to claim 8, wherein the cancer is leukemia, lymphoma, gliosarcoma, melanoma or bone marrow cancer.

11. A method of making a compound of the formula:

Structure A wherein:

$R_1$ is $(CH_2)_2OH$ and $R_2$ is $(CH_2)_2SB_xH_y$; where x is 9 to 12; and y is x−1 or $R_1$ and $R_2$ when taken together with the associated nitrogen atom are:

Structure B where x is 9 to 12 and y is x−1, comprising contacting an amount of a nitrogen mustard derivative with an amount of sodium borocaptate ($Na_2B_{12}H_{11}SH$) sufficient to yield said compound.

12. A method of making a compound of the formula:

Structure C or Structure D comprising contacting an amount of melphalan with an amount of sodium borocaptate ($Na_2B_{12}H_{11}SH$) sufficient to yield said compound.

13. A method according to claim 11, wherein merphalan and sodium borocaptate are dissolved in an amount of sodium bicarbonate solution sufficient to yield said compound.

14. A method according to claim 12, wherein melphalan and sodium borocaptate are dissolved in an amount of sodium bicarbonate solution sufficient to yield said compound.

15. A compound of the formula:

Structure A wherein:

$R_1$ is $CH_2)_2OH$ and $R_2$ is $(CH_2)_2SB_xH_y$; where x is 9 to 12; and y is x−1 or $R_1$ and $R_2$ when taken together with the associated nitrogen atom are:

Structure B where x is 9 to 12 and y is x−1, prepared by contacting an amount of a nitrogen mustard derivative with an amount of sodium borocaptate ($Na_2B_{12}H_{11}SH$) sufficient to yield said compound.

16. A compound of the formula:

Structure C or Structure D prepared by contacting an amount of melphalan in an amount of sodium borocaptate ($Na_2B_{12}H_{11}SH$) sufficient to yield said compound.

17. A compound prepared according to claim 15, wherein melphalan and sodium borocaptate are dissolved in an amount of sodium bicarbonate solution sufficient to yield said compound.

18. A compound prepared according to claim 16, wherein melphalan and sodium borocaptate are dissolved in an amount of sodium bicarbonate solution sufficient to yield said compound.

19. A method of treating a mammal having a tumor, comprising administering to the mammal a therapeutically effective amount of a compound prepared according to claim 15 and irradiating the mammal with neutron radiation.

20. A method of treating a mammal having a tumor, comprising administering to the mammal a therapeutically effective amount of a compound prepared according to claim 16 and irradiating the mammal with neutron radiation.

21. A method according to claim 19, wherein the compound is administered orally, parenterally or topically to the mammal.

22. A method according to claim 20, wherein the compound is administered orally, parenterally or topically to the mammal.

23. A method according to claim 19, wherein the tumor is a cancer.

24. A method according to claim 20, wherein the tumor is a cancer.

25. A method according to claim 23, wherein the cancer is leukemia, lymphoma, gliosarcoma, melanoma or bone marrow cancer.

26. A method according to claim 24, wherein the cancer is leukemia, lymphoma, gliosarcoma, melanoma or bone marrow cancer.

27. A method of treating a mammal having a bone marrow tumor, comprising administering to the bone marrow tumor ex vivo, a therapeutically effective amount of a compound of the formula:

Structure A wherein:

$R_1$ is $(CH_2)_2OH$ and $R_2$ is $(CH_2)_2SB_xH_y$; where x is 9 to 12; and y is x−1 or $R_1$ and $R_2$ when taken together with the associated nitrogen atom are:

Structure B where x is 9 to 12 and y is x−1 and irradiating the bone marrow tumor ex vivo with neutron radiation.

28. A method of treating a mammal having a bone marrow tumor, comprising administering to the bone marrow tumor ex vivo, a therapeutically effective amount of a compound of the formula:

Structure C or Structure D and irradiating the bone marrow tumor ex vivo with neutron radiation.

29. A method according to claim 27, wherein the tumor is a cancer.

30. A method according to claim 28, wherein the tumor is a cancer.

31. A method according to claim 29, wherein the cancer is leukemia or lymphoma.

32. A method according to claim 30, wherein the cancer is leukemia or lymphoma.

* * * * *